(12) United States Patent
Kontani

(10) Patent No.: US 8,362,173 B2
(45) Date of Patent: Jan. 29, 2013

(54) POLYMER CAPABLE OF ADSORBING ACIDIC WATER-SOLUBLE TARGET SUBSTANCE, AND METHOD FOR PRODUCTION OF THE POLYMER

(75) Inventor: Tomohiro Kontani, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 311 days.

(21) Appl. No.: 12/918,887

(22) PCT Filed: Dec. 2, 2008

(86) PCT No.: PCT/JP2008/071906
§ 371 (c)(1),
(2), (4) Date: Aug. 23, 2010

(87) PCT Pub. No.: WO2009/104323
PCT Pub. Date: Aug. 27, 2009

(65) Prior Publication Data
US 2011/0003937 A1    Jan. 6, 2011

(30) Foreign Application Priority Data

Feb. 21, 2008    (JP) ................ P2008-040189

(51) Int. Cl.
*C08F 20/60*    (2006.01)
*C08F 20/34*    (2006.01)

(52) U.S. Cl. ........................ 526/307; 526/310

(58) Field of Classification Search .......... 526/307, 526/310
See application file for complete search history.

(56) References Cited

U.S. PATENT DOCUMENTS
2004/0059065 A1    3/2004    Goto et al.

FOREIGN PATENT DOCUMENTS

| | | |
|---|---|---|
| DE | 199 31 720 A1 | 1/2001 |
| JP | 2003-509550 A | 3/2003 |
| JP | 2003-513112 A | 4/2003 |
| JP | 2003-514051 A | 4/2003 |
| JP | 2004-018576 A | 1/2004 |
| JP | 2004-131406 A | 4/2004 |
| JP | 2006-028467 A | 2/2006 |
| JP | 2006-137805 A | 6/2006 |
| JP | 2007-532715 A | 11/2007 |
| JP | 2008-500442 A | 1/2008 |
| WO | 2002-022698 A1 | 3/2002 |
| WO | 2006-067431 A1 | 6/2006 |
| WO | 2006-129088 A1 | 12/2006 |
| WO | 2007-023915 A1 | 3/2007 |
| WO | 2007/136756 A2 | 11/2007 |

OTHER PUBLICATIONS

Chinese Office Action issued on Feb. 16, 2012 in the corresponding Chinese Patent Application No. 200880127248.7.
International Search Report (PCT/ISA/210), for PCT/JP2008/071906, dated Mar. 10, 2009.

(Continued)

*Primary Examiner* — Vu A Nguyen
(74) *Attorney, Agent, or Firm* — Sughrue Mion, PLLC

(57) ABSTRACT

To provide a polymer which selectively adsorbs an acidic water-soluble target substance, a polymer which has a specific recognition site for an acidic water-soluble target substance, a production process thereof, and an acidic water-soluble target substance-adsorbing agent.

A polymer which selectively adsorbs at least one kind of an acidic water-soluble target substance, in which the polymer has a cross-linked structure formed through a two-step reaction including a Michael addition reaction of a polymer having an amino group and/or imino group with an unsaturated carbonyl cross-linker, and a subsequent radical polymerization.

24 Claims, 1 Drawing Sheet

OTHER PUBLICATIONS

European Search Report dated Apr. 18, 2011, Issued in Application No. 08872579.1.

Chinese Office Action issued on Sep. 26, 2011 in corresponding Chinese Patent Application No. 200880127248.7.
European Office Action issued on Oct. 12, 2011 in corresponding European Application No. 08872579.1.

POLYMER CAPABLE OF ADSORBING ACIDIC WATER-SOLUBLE TARGET SUBSTANCE, AND METHOD FOR PRODUCTION OF THE POLYMER

TECHNICAL FIELD

The invention relates to: a polymer which selectively adsorbs an acidic water-soluble target substance; a polymer which has a specific recognition site for an acidic water-soluble target substance; a production process thereof; and an acidic water-soluble target substance-adsorbing agent.

BACKGROUND ART

Selective separation techniques for a target substance based on the structure and characteristics of the target substance is a technique essential for various industries and chemical and biological studies and the like. In the selective separation techniques, a molecular imprinting method is one of the most important methods (e.g., see Non-patent Reference 1). A molecularly imprinted polymer obtained by the molecular imprinting method (to be referred also to as MIP hereinafter) has a characteristic of having a specific binding site complementary to a template molecule, which is effected by the polymerization of a polymerizable molecule having a functional group in the presence of the template molecule and subsequent removal of the template molecule.

As a substitute for a biological antibody, for example, application of MIP to a chromatographic separation of medical substances, a solid phase extraction of environment-derived or organism-derived samples for pretreatment, an artificial antibody for immunoassay and a biosensor device for the detection of structural specificity and the like has so far been examined.

In general, preparation of MIP is carried out making use of an interaction by hydrogen bond in an organic solvent. Thus, it is difficult to prepare an MIP for a water-soluble compound in an organic solvent. Also, when an MIP prepared in an organic solvent is used in an aqueous solution, it poses a problem of reducing its specific binding ability for the template molecule of MIP due to shrinking of the polymer. Further, since water molecule has a characteristic of dissociating hydrogen bond between substances, it is markedly difficult to prepare and use MIP in water. In addition, there is a tendency of causing nonselective adsorption to the surface of polymer matrix in aqueous solution due to a hydrophobic interaction.

In recent years, those which were prepared using acryloyl cyclodextrin and bis-acrylamide (cf. Non-patent Reference 2) and those which were prepared using polyethylene glycol diacrylate by an inter-functional group distance immobilization method (cf. Patent Reference 1), as novel MIPs prepared in an aqueous solution, have been reported. These MIPs show a certain degree of selective adsorption for template molecules.

However, since MIP is produced using excess amount of a functional monomer in the production method of Non-patent Reference 1, it is considered that recognition sites for the template molecule of MIP are not uniform. Also, since MIP is produced by forming an ionic interaction in an organic solvent in the production method of Patent Reference 1, it is considered that the distance between functional groups in the organic solvent is different from the distance between functional groups in aqueous solution. Accordingly, it is considered that the imprint effect is not sufficient by these methods. In addition, these methods have a problem in that they cannot be applied to a water-soluble compound which does not have an aromatic or the like hydrophobic backbone.

By the way, the number of chronic dialysis patients has exceeded 200,000 in recent years; with a tendency of increasing every year. Regardless of the presence of such a large number of chronic renal insufficiency patients, there is no fundamental therapeutic method and it is the present situation that there is only a blood dialysis as a symptomatic therapy aimed at prolonging life. As the blood dialysis therapy for renal insufficiency, it is general to remove uremia related substances and the like toxic substances produced and accumulated in the blood of patients, using a hollow fiber membrane type artificial kidney which uses a cellulose-based natural polymer and polysulfone, methyl polymethacrylate and the like synthetic polymer as the material.

The hollow fiber membrane wall is prepared in such a manner that fine pores having a diameter of approximately from 10 to 100 nm penetrate through it, and the toxic substances are transferred from the blood side to the dialysate side through the pores by the osmotic pressure difference. Currently, performance of the hollow fiber membranes has been markedly improved, thus rendering possible removal of not only urea, creatinine and the like low molecular weight substances (500 daltons or less) but also medium molecular weight substances (500 to 5,000 daltons) or low molecular weight proteins having a molecular weight of 10,000 daltons or more from renal insufficiency patients by dialysis.

However, a hollow fiber membrane capable of removing causal substances having large molecular weights has a tendency that hormones, vitamins, amino acids and water which are essential for the living body are excessively discharged into outside of the body, based on the engineering ground of structure and permeability of the membrane. Accordingly, when the dialysis is carried out for a prolonged period of time, it generates bone and joint disorders, anemia, blood pressure reduction and the like various complications caused thereby.

As described in the above, the current method for treating renal insufficiency by a hollow fiber membrane has many insufficient points in terms of the selective solute-removing ability and has a problem in that the low molecular weight substances essential for the living body are also discharged from the body by the dialysis. However, a countermeasure for this problem of dialysis has not so far been found. In addition, since compulsory time for patients at the hospital is very long in the case of general blood dialysis, there is also a problem in that burden on the social activities is large.

Non-patent Reference 1: B. Sellergren, Molecularly imprinted polymers: man made mimic of antibodies and their application, Elsevier Science (2001)

Non-patent Reference 2: H. Asanuma, T. Akiyama, K. Kajiyama, T. Hishiya and N. Komiyama, Anal. Chim. Acta, 2001, 435, 25

Patent Reference 1: JP-A-2006-137805

DISCLOSURE OF THE INVENTION

Problems that the Invention is to Solve

By taking the above problems into consideration, the invention contemplates providing: a polymer which selectively adsorbs uric acid, creatine and the like nitrogenous metabolic waste products, nucleoside, amino acids and the like acidic water-soluble target substance; a polymer which has a specific recognition site for an acidic water-soluble target substance; a production process thereof; and an acidic water-soluble target substance-adsorbing agent.

Means for Solving the Problems

With the aim of solving the aforementioned problems, the present inventors have conducted intensive studies and found as a result that a polymer, which has a cross-linked structure formed through a two-step reaction including a Michael addition reaction of a polymer having an amino group and/or imino group with an unsaturated carbonyl cross-linker and a subsequent radical polymerization, can selectively adsorb an acidic water-soluble target substance.

In addition, it was found that a polymer prepared through a two-step reaction including a Michael addition reaction of a polymer having an amino group and/or imino group with an unsaturated carbonyl cross-linker and a subsequent radical polymerization, in combination with a molecular imprinting method, has high affinity for an acidic water-soluble target substance and can specifically recognize the acidic water-soluble target substance and adsorb it, thereby resulting in the accomplishment of the invention. That is, the invention is as follows.

1. A polymer which selectively adsorbs at least one kind of an acidic water-soluble target substance, in which the polymer has a cross-linked structure formed through a two-step reaction including a Michael addition reaction of a polymer having an amino group and/or imino group with an unsaturated carbonyl cross-linker, and a subsequent radical polymerization.

2. A polymer containing a specific recognition site for at least one kind of an acidic water-soluble target substance, in which the specific recognition site is formed in an aqueous solution by a molecular imprinting method including the following steps (1) and (2):

(1) a step of forming a cross-linked copolymer through a two-step reaction including a Michael addition reaction of at least one kind of a polymer having an amino group and/or imino group and being capable of interacting with the template molecule with an unsaturated carbonyl cross-linker, and a subsequent radical polymerization, in the presence of at least one kind of a template molecule; and (2) a step of carrying out a release removal of the template molecule from the cross-linked copolymer obtained in step (1), thereby forming the specific recognition site for the template molecule.

3. The polymer described in the aforementioned item 2, in which the template molecule is an acidic water-soluble target substance or a dummy molecule of the acidic water-soluble target substance.

4. The polymer described in any one of the aforementioned items 1 to 3, in which the polymer having an amino group and/or imino group is a polymer modified with at least one kind of a functional group capable of interacting with the acidic water-soluble target substance.

5. The polymer described in the aforementioned item 4, in which the functional group capable of interacting with the acidic water-soluble target substance is any one of a diaminotriazine derivative, a diaminopyridine derivative, a guanidine derivative, an imidazole derivative, a porphyrin derivative and a cyclodextrin derivative.

6. The polymer described in any one of the aforementioned items 1 to 5, in which the acidic water-soluble target substance is any one of a nitrogenous metabolic waste product, nucleotide and an amino acid.

7. The polymer described in the aforementioned item 6, in which the nitrogenous metabolic waste product is uric acid.

8. The polymer described in any one of the aforementioned items 1 to 7, in which the unsaturated carbonyl cross-linker has two or more unsaturated carbonyl groups.

9. The polymer described in the aforementioned item 8, in which a molar ratio of the amino group and/or imino group to the unsaturated carbonyl groups is in a range of from 0.15 to 1.35.

10. The polymer described in any one of the aforementioned items 2 to 9, which is capable of partially bonding with the acidic water-soluble target substance through the specific recognition site.

11. The polymer described in any one of the aforementioned items 1 to 10, which selectively adsorbs the acidic water-soluble target substance in an aqueous solution.

12. A process for producing a polymer which selectively adsorbs at least one kind of an acidic water-soluble target substance, in which the process includes forming a cross-linked copolymer through a two-step reaction including a Michael addition reaction of at least one kind of a polymer having an amino group and/or imino group and being capable of interacting with the acidic water-soluble target substance with an unsaturated carbonyl cross-linker, and a subsequent radical polymerization.

13. A process for producing a polymer containing a specific recognition site for at least one kind of an acidic water-soluble target substance, the process comprising forming the specific recognition site in an aqueous solution by a molecular imprinting method including the following steps (1) and (2):

(1) a step of forming a cross-linked copolymer through a two-step reaction including a Michael addition reaction of at least one kind of a polymer having an amino group and/or imino group and being capable of interacting with the template molecule with an unsaturated carbonyl cross-linker, and a subsequent radical polymerization, in the presence of at least one kind of a template molecule; and (2) a step of carrying out a release removal of the template molecule from the cross-linked copolymer obtained in step (1), thereby forming the specific recognition site for the template molecule.

14. The process for producing a polymer described in the aforementioned item 12 or 13, in which the polymer having an amino group and/or imino group has, other than the amino group and/or imino group, at least one kind of a functional group capable of partially bonding with the acidic water-soluble target substance.

15. An acidic water-soluble target substance-adsorbing agent which includes the polymer described in any one of the aforementioned items 1 to 11.

16. A method for selectively separating or removing an acidic water-soluble target substance using the polymer described in any one of the aforementioned items 1 to 11.

Advantage of the Invention

The polymer of the invention has excellent adsorbing property for an acidic water-soluble target substance and exerts the property to more selectively adsorb the acidic water-soluble target substance alone even in a living body-resembling environment, so that it is possible to exclude the acidic water-soluble target substance alone quickly without removing living body essential components. Accordingly, since an acidic water-soluble target substance-adsorbing agent including the polymer of the invention as the main component enables suppression of reduction of blood nutritive components that leads to a complication as well as alleviation of the burden on social activities, in comparison with the conventional blood dialysis, it is markedly useful as a substitute for the dialysis therapy.

BEST MODE FOR CARRYING OUT THE INVENTION

Figure 1:
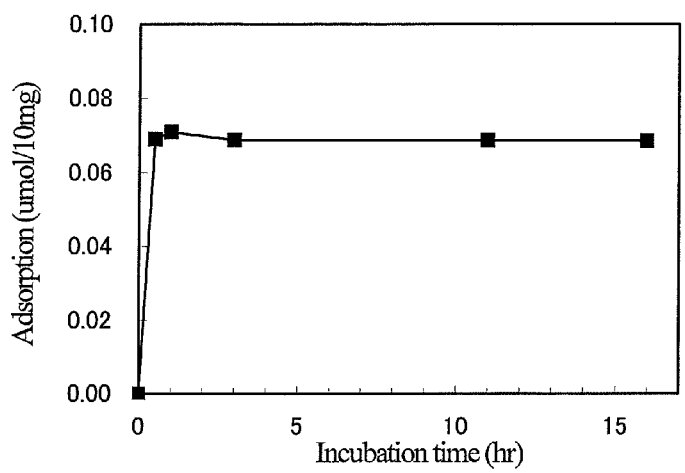
FIG. 1 shows uric acid adsorption rate by the polymer of Inventive Example 1-1.

The invention provides a polymer which selectively adsorbs an acidic water-soluble target substance. Here, the "acidic water-soluble target substance" as used in the present invention means a water-soluble compound which contains an acidic functional group. As the acidic functional group, for example, phosphate group, sulfone group, carboxyl group, hydroxyl group, imino group, amido group, ester group, urethane group and the like can be cited.

As the aforementioned acidic water-soluble target substance, for example, uric acid, creatinine, bilirubin and the like nitrogenous metabolic waste products (waste matter formed by the metabolism of nitrogen-containing compounds), hippuric acid and the like metabolites, uridine, cytidine, adenosine, guanosine and the like nucleosides, a nucleoside 5'-mono-phosphorylated nucleotide, a polynucleotide or oligonucleotide as a nucleotide copolymer, a nucleoside 5'-di-phosphorylated nucleoside diphosphate, a nucleoside 5'-tri-phosphorylated nucleoside triphosphate, aspartic acid, tyrosine, serine, alanine and the like amino acid, a polypeptide or oligopeptide consisting of amino acid residues, cholic acid and the like bile acid, 2,4-dichlorophenoxy acetate and the like agricultural chemicals, and bisphenol A and the like endocrine disrupting chemicals and the like can be cited.

In addition, the dummy molecule of an acidic water-soluble target substance means a molecule in which its main backbone is the same or analogous and the backbone containing a functional group capable of interacting with other molecule is the same or analogous. For example, UMP (uridine 5'-monophosphate) and AMP (adenosine 5'-monophosphate) have the same main pentose backbone and have the same phosphate group contributing to the interaction, so that both are dummy molecules.

When the polymer of the invention is used as a substitute for the dialysis therapy of chronic renal insufficiency, it is desirable that the acidic water-soluble target substance is nitrogenous metabolic waste product, preferably uric acid.

The term "selectively adsorb" according to the invention means to adsorb a target substance preferentially. The selective adsorption for an acidic water-soluble target substance by the polymer of the invention can be measured based on the measurement of absorbance by a spectrophotometer, elution rate by a high performance liquid chromatography and the like.

The polymer of the invention which selectively adsorbs an acidic water-soluble target substance has a cross-linked structure formed through a two-step reaction including a Michael addition reaction of a polymer having an amino group and/or imino group with an unsaturated carbonyl cross-linker (first stage reaction), and a subsequent radical polymerization (second stage reaction). By allowing a polymer having an amino group and/or imino group and an unsaturated carbonyl cross-linker to undergo their cross-linking through the two-step reaction, a cross-linked copolymer having a rigid and high performance specific recognition site can be obtained.

[First Stage Reaction: Michael Addition Reaction]

In the Michael addition reaction method as the first stage reaction, a polymer having an amino group and/or imino group, an unsaturated carbonyl cross-linker and the like reaction components and a template molecule are dissolved in a polymerization solvent, and then the polymer having an amino group and/or imino group and the unsaturated carbonyl cross-linker are allowed to undergo the addition reaction, thereby obtaining a cross-linked copolymer.

The Michael addition reaction is generally carried out by combining a polymer solution prepared by dissolving a polymer having an amino group and/or imino group in a polymerization solvent and a cross-linker solution prepared by dissolving an unsaturated carbonyl cross-linker in the polymerization solvent, stirring the mixture, and then allowing them to undergo the reaction through standing in the dark. The stirring method and time are not particularly limited, and complete mixing is the goal. Reaction temperature of the Michael addition reaction is preferably from 4 to 90° C., more preferably from 4 to 35° C. In addition, the reaction time is preferably 1 hour or more, more preferably 12 hours or more (generally 48 hours or less).

(Polymer Having an Amino Group and/or Imino Group)

The polymer of the invention can interact with an acidic water-soluble target substance owing to a possession of an amino group and/or imino group. As the polymer having an amino group and/or imino group, for example, an allylamine-based polymer which uses allylamine having primary and/or secondary amino group as the monomer (e.g., a polyallylamine, a polyallylamine in which the amino group is partially acetylated or alkylated and the like), an alkylene imine-based polymer, a vinylamine-based polymer, a lysine-based polymer, chitosan, a polymer having two or more of primary and/or secondary amino group or imino group and the like can be cited.

Among the aforementioned polymers having an amino group and/or imino group, a polyallylamine having a weight average molecular weight of 20,000 or less, preferably 18,000 or less (generally 1,000 or more) is appropriately used from the viewpoint of efficiently carrying out the Michael addition reaction and efficiently expressing electrostatic interaction with the acidic water-soluble target substance. The polymer having an amino group and/or imino group may be used alone or as a combination of two or more species.

According to the invention, it is desirable that the polymer having an amino group and/or imino group is used as a polymer solution by dissolving it in a polymerization solvent, and the polymer solution is made into a Michael addition reaction solution by combining it with a cross-linker solution prepared by dissolving an unsaturated carbonyl cross-linker in the polymerization solvent. Polymer concentration in the polymer solution is preferably from 5 to 40% by mass, more preferably from 5 to 20% by mass. When the polymer concentration is larger than 40% by mass, the solution viscosity becomes so high that the handling becomes difficult.

In addition, it is desirable that concentration of the polymer having an amino group and/or imino group in the Michael addition reaction solution is set to a range of from 2 to 15% by mass, more desirably from 3 to 6% by mass.

(Unsaturated Carbonyl Cross-Linker)

Owing to the cross-linking of an amino group and/or imino group with an unsaturated carbonyl cross-linker by Michael addition reaction, the polymer of the invention not only can form a specific recognition site for an acidic water-soluble target substance but also can cap the amino group and/or imino group which is/are not required by the specific recognition site. Then, it becomes possible to suppress nonselective adsorption due to excess functional groups.

It is desirable that the aforementioned unsaturated carbonyl cross-linker is a compound which has two or more unsaturated carbonyl groups. As such an unsaturated carbonyl cross-linker, for example, N,N'-bisacryloylpiperazine, N,N'-ethylenebisacrylamide, N,N'-methylenebisacrylamide, polyethylene glycol di(meth)acrylate, ethylene glycol di(meth)acrylate, trimethylolpropane trimethacrylate and the like can be cited. The unsaturated carbonyl cross-linker may be used alone or as a combination of two or more species.

Although the blending ratio of the aforementioned amino group and/or imino group with unsaturated carbonyl cross-linker is not particularly limited, the molar ratio of (amino group and/or imino group)/(unsaturated carbonyl group of unsaturated carbonyl cross-linker) is set preferably from 0.15 to 1.35, more preferably from 0.25 to 0.66.

When the aforementioned molar ratio of (amino group and/or imino group)/(unsaturated carbonyl group of unsaturated carbonyl cross-linker) is larger than 1.35, the amino group and/or imino group cannot react sufficiently with the unsaturated carbonyl group, thus causing a tendency of increasing adsorption of the living body essential components by the residual amino group and/or imino group. In this connection, when the molar ratio is smaller than 0.15, the number of amino groups and/or imino groups capable of forming the specific recognition site in the polymer becomes small, thus causing a tendency that selective adsorption of the acidic water-soluble target substance cannot be exerted.

In addition, in order to improve adsorption selectivity of the obtained polymer of the invention, as occasion demands, an unsaturated carbonyl compound other than the unsaturated carbonyl cross-linker may be allowed to undergo the reaction simultaneously with or after the Michael addition reaction. As such an unsaturated carbonyl compound, for example, 2-hydroxyethyl(meth)acrylate, glycerol(meth)acrylate, N-vinyl pyrrolidone, acrylamide, an alkyl(meth)acrylate and the like can be cited.

(Polymerization Solvent)

As the polymerization solvent, for example, water, methanol, ethanol and the like alcohols, and dimethyl formamide and the like organic solvents and the like can be cited, of which water is desirable. By the use of aqueous solution as the solvent, a highly hydrophilic polymer can be obtained and nonselective adsorption by a hydrophobic interaction can be suppressed. The polymerization solvent may be used alone or as a combination of two or more species.

Concentration of the polymerization solvent in the Michael addition reaction solution is not particularly limited, but it is desirable to use it at a ratio of from 1 to 9 as the aforementioned (total amount of the polymerization solvent used in the polymer solution and cross-linker solution described in the above)/(total amount of the unsaturated carbonyl cross-linker and polymer having an amino group and/or imino group). When total amount ratio of the polymerization solvent is large, there is a tendency that adsorption of the living body essential components is increased.

The polymerization solvent contains a polymerization initiator. The polymerization initiator is not particularly limited with the proviso that it is a radical polymerization initiator which forms radical by activating vinyl group, and for example, azo-compounds such as 2-2' azobis(2-amindino-propane) dihydrochloride, 2,2'-azobis(N,N'-dimethyl-eneisobutylamidine) dihydrochloride, 2,2'-azobis[2-(N-allylamidino)propane] disulfate, 2,2'-azobis[2-methyl-N-(2-hydroxyethyl)-propionamide], 4,4'-azobis(4-cyanopentanoate) and the like, persulfates such as sodium persulfate, ammonium persulfate and the like, and organic peroxides such as t-butyl peroxide, disuccinate peroxide and the like can be cited. These polymerization initiators may be used alone or as a combination of two or more species. In addition, these polymerization initiators may be used together with, for example, N,N,N',N'-tetramethylethylenediamine or the like polymerization accelerator.

Blending ratio of the polymerization initiator and the unsaturated carbonyl cross-linker is not particularly limited, but it is desirable that the molar ratio of the polymerization initiator/unsaturated carbonyl cross-linker is from 0.0025 to 0.02 in order to obtain the polymer with sufficient rate of polymerization, and is from 0.004 to 0.01 in order to obtain more rigid and high-performance cross-linked copolymer.

[Second Stage Reaction: Radical Polymerization Reaction]

In the radical polymerization method as the second stage reaction, a cross-linked copolymer is obtained after completion of the Michael addition reaction, by allowing the Michael addition reaction solution to undergo radical polymerization. By this, the polymer of the invention can realize high selective adsorption for the acidic water-soluble target substance in an aqueous solution.

The aforementioned radical polymerization reaction can use a conventionally known method and can be carried out, for example, by heating at from 40 to 120° C. or irradiating ultraviolet ray, electron beam or the like active energy ray. As the active energy ray, ultraviolet ray is preferable.

When the radical polymerization is carried out by ultraviolet ray irradiation, the reaction is effected by standing in the dark after ultraviolet ray irradiation. In this case, it is desirable to set the reaction temperature to a range of from 4 to 90° C., more desirably to a range of from 4 to 15° C. In addition, the reaction time is preferably 12 hours or more, more preferably 18 hours or more (generally 36 hours or less).

The cross-linked copolymer obtained in the above manner may be used by pulverizing it using ball mill, hammer mill, jet mill, mortar or the like method and then recovering specified size of the product. In addition, shape of the cross-linked copolymer is not particularly limited, and the pulverized product may be recovered, or it may be polymerized in advance into a specific form of particle by employing a conventionally known particle production method such suspension polymerization, dispersion polymerization or the like method.

The invention also provides a polymer which has a specific recognition site for an acidic water-soluble target substance. In this case, the "specific recognition site" is a site which corresponds to the template of the acidic water-soluble target substance that becomes the recognizing object of the polymer, and it means a porous region complementary to the acidic water-soluble target substance as the object substance.

As is described later, the aforementioned specific recognition site is formed by a molecular implanting method. By this, the specific recognition site has high affinity for the acidic water-soluble target substance even under a living body-resembling environment, and the polymer of the invention having a specific recognition site for the acidic water-soluble target substance can express a specific acidic water-soluble target substance-recognizing ability.

In addition, the polymer of the invention having a specific recognition site for the acidic water-soluble target substance has a markedly good fitness to aqueous media and can quickly attain adsorption with a specified acidic water-soluble target substance.

Regarding the polymer of the invention having a specific recognition site for the acidic water-soluble target substance, the specific recognition site is formed in an aqueous solution by a molecular imprinting method which includes the following: step (1) for obtaining a cross-linked copolymer through a two-step reaction including a Michael addition reaction and a radical polymerization; and step (2) for forming a specific recognition site for a template molecule.

In this case, as described in the foregoing, the "molecular imprinting method" is a method in which a polymer having a specific binding site complementary to a template molecule is prepared by carrying out polymerization of a polymerizable molecule having a functional group in the presence of the template molecule and subsequently removing the template molecule.

According to the invention, the molecular imprinting method is carried out in an aqueous solution. Preferred polymerization solvent as an aqueous solution is, for example, a solvent which does not spoil interaction of the polymer having an amino group and/or imino group with an acidic water-soluble target substance as the template molecule, can dissolve respective polymerization components and also can become a solvent for obtaining porosity (porogen).

As the aforementioned polymerization solvent, as described in the above, for example, water, methanol, ethanol and the like alcohols, and dimethyl formamide and the like organic solvents and the like can be cited, of which water is desirable from the viewpoint of blood, body fluid and the like environment when used. The polymerization solvent may be used alone or as a combination of two or more species.

The aforementioned steps (1) and (2) are described in the following. Step (1) for obtaining a cross-linked copolymer through a two-step reaction including a Michael addition reaction and a radical polymerization This step is a step for obtaining a cross-linked structure through a two-step reaction including a Michael addition reaction of at least one kind of a polymer having an amino group and/or imino group and being capable of interacting with the template molecule with an unsaturated carbonyl cross-linker, and a subsequent radical polymerization, in the presence of at least one kind of a template molecule.

The aforementioned "template molecule" means an acidic water-soluble target substance. In addition, as the aforementioned "interaction", for example, intermolecular interactions by ionic bond, hydrogen bond, van der Waals force, coordinate bond, electrostatic interaction, dipole interaction, π-π stacking and the like can be cited.

The amino group and/or imino group in the aforementioned polymer can function as an interaction point of the specific binding site by interacting with the template molecule. In addition, when the amino group and/or imino group reacts with an unsaturated carbonyl cross-linker that can be subjected to a Michael addition reaction, the amino group and/or imino group which is/are not necessary for the specific recognition site can function as a cross-linking point. Thus, the polymer of the invention having a specific recognition site for an acidic water-soluble target substance not only suppresses nonselective adsorption but also can exert high selective adsorption ability for the acidic water-soluble target substance.

The aforementioned polymer may also have at least one kind of functional group capable of interacting with the acidic water-soluble target substance, other than amino group and/or imino group. Accordingly, it becomes possible to interact with the aforementioned target substance at multiple points and also specifically, and higher selective adsorption ability for the aforementioned target substance can be exerted in comparison with the case of the use of the amino group and/or imino group alone.

As the functional group capable of partially bonding with the aforementioned acidic water-soluble target substance, it is not particularly limited with the proviso that it can interact with the target substance but, for example, a diaminotriazine derivative, a diaminopyridine derivative, a guanidine derivative, an imidazole derivative, a porphyrin derivative, a cyclodextrin derivative, a pyridine derivative, a pyrimidine derivative, a triazole derivative, a pyrrole derivative, an indole derivative, a purine derivative, an amide derivative and the like can be cited.

The aforementioned functional group may be any substituent group which has the backbone of the corresponding compound, and among them, a diaminotriazine derivative [the following formula (1)], a diaminopyridine derivative [the following formula (2)], a guanidine derivative [the following formula (3)], an imidazole derivative [the following formula (4)], a porphyrin derivative [the following formula (5)] and a cyclodextrin derivative [the following formula (6)] are particularly desirable, and a diaminotriazine derivative capable of interacting with imido group at multiple points is more desirable (e.g., a 2,4-diamino-s-triazine derivative).

[Chem. 1]

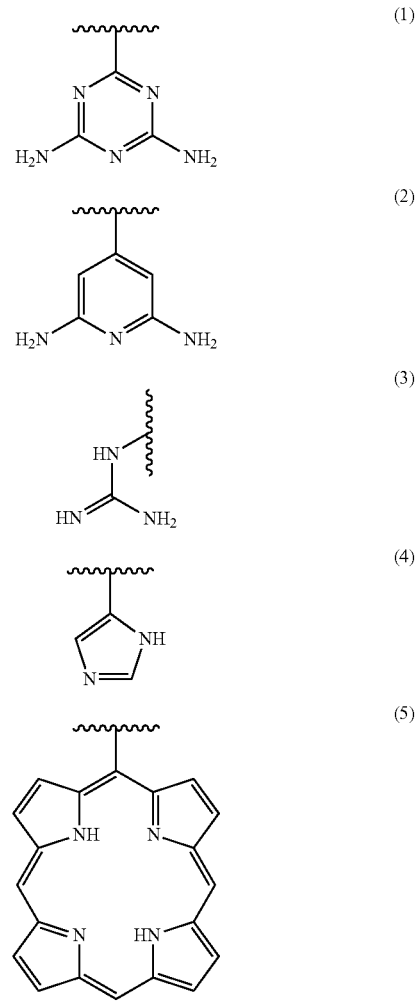

-continued

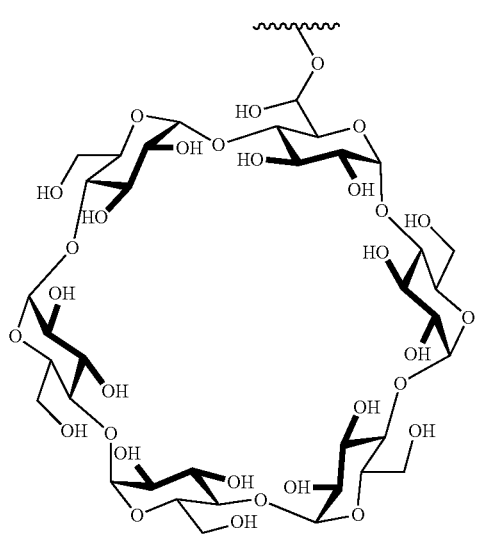

(6)

In the step (1), it is desirable to set the molar ratio of acidic water-soluble target substance/(amino group and/or imino group) to 0.05 or more, more desirably from 0.075 to 0.125. When the molar ratio is smaller than 0.05, the number of existing specific recognition sites in the polymer becomes small, thus showing a tendency that selective adsorption of the acidic water-soluble target substance cannot be exerted.

Step (2) for Forming a Specific Recognition Site for a Template Molecule

The step (2) is a step of carrying out a release removal of the template molecule from the cross-linked copolymer obtained in the step (1) thereby forming the specific recognition site for the template molecule.

As the method for carrying out a release removal of an acidic water-soluble target substance as the template molecule from the cross-linked polymer, for example, a method for washing with a hydrophilic solvent can be cited. As the hydrophilic solvent, for example, a sodium hydroxide aqueous solution, pyridine, dimethylformamide, methanol, ethanol, acetone, water and the like can be cited. These solvents may be used alone or as a combination of two or more species.

As an illustrative example of the method for carrying out a release removal of an acidic water-soluble target substance from the cross-linked polymer, for example, a method which includes the following steps (a) and (b) can be cited.

(a) When a sodium hydroxide aqueous solution is used, the cross-linked polymer is mixed with 0.5 mol/l sodium hydroxide aqueous solution and stirred, and washed by repeatedly exchanging the liquid until the acidic water-soluble target substance becomes undetectable in the supernatant.

(b) An acidic water-soluble target substance-specific recognition polymer is obtained by substituting the solution with ultrapure water, repeatedly exchanging the liquid until pH of the supernatant fluid becomes 7 or less thereby effecting desalting, and then carrying out freeze-drying.

In addition, a method which includes the following steps (A) to (D) is described as an illustrative example for further minutely describing the steps for obtaining the polymer by the method of the invention, though the steps for obtaining the polymer are not limited to this illustrative example.

(A) Generally 75 mmol/l or more, preferably 100 mmol/l or more of an acidic water-soluble target substance (e.g., uric acid) and generally from 5 to 40% by mass, preferably from 5 to 20% by mass of polyallylamine as the polymer having an amino group and/or imino group are dissolved in water to be used as the polymerization solvent thereby preparing a polymer solution.

(B) A cross-linker solution is prepared by dissolving an unsaturated carbonyl cross-linker (e.g., N,N'-bisacryloylpiperazine) and an polymerization initiator [e.g., 2,2'-azobis(2-amidinopropane) dihydrochloride] in water as the polymerization solvent.

(C) The first step crosslinking reaction by the Michael addition reaction is carried out by adding the cross-linker solution prepared in (B) to the polymer solution prepared in (A), stirring the mixture for 30 seconds and then allowing it to stand at room temperature for 16 hours in the dark.

(D) The second step crosslinking reaction by the radical polymerization reaction is carried out by irradiating ultraviolet ray at 4° C. for 24 hours. After the reaction, the bulk cross-linked copolymer is pulverized by ball mill.

It is desirable that the polymer of the invention can bond partially with an acidic water-soluble target substance through a specific recognition site. By the ability to bond partially with the acidic water-soluble target substance, it becomes possible to design such that the polymer of the invention can bond also with two or more acidic water-soluble target substances, so that the acidic water-soluble target substances can be adsorbed more efficiently.

The invention provides an acidic water-soluble target substance-adsorbing agent which contains the polymer of the invention. The adsorbing agent of the invention contains, as the main component, a polymer of the invention capable of selectively adsorbing an acidic water-soluble target substance or a polymer having a specific recognition site for the acidic water-soluble target substance, and may be mixed with one or more adsorbent which is physically or chemically suitable. As such an adsorbent, for example, activated carbon, activated carbon fiber, carbon black, silica gel, activated alumina, zeolite and the like can be cited.

When the adsorbing agent of the invention is used in adsorbing an acidic water-soluble target substance, though not particularly limited, for example, an acidic water-soluble target substance alone can be selectively separated or removed by using the adsorbing agent as a filler of an adsorber and adding a solution containing the acidic water-soluble target substance to the filler.

In addition, when the adsorbing agent is added to a solution containing an acidic water-soluble target substance and the acidic water-soluble target substance-adsorbed adsorbing agent is removed by filtration or decantation, the acidic water-soluble target substance can also be selectively separated or removed from the solution.

EXAMPLES

The following describes the invention further in detail with reference to examples, but the invention is not limited to these examples alone.

Inventive Example 1-1

[Preparation of Polymer Solution]

In a screw glass test tube, 36.0 mg (0.21 mmol) of uric acid (Sigma Aldrich) was added to 1.2 ml of an aqueous solution of polyallylamine having a molecular weight of 15,000 (total amount of amino groups per 1 g, 17.5 mmol) (mfd. by NITTO BOSEKI) (PALA 15) prepared into 10% by mass (amino group 2.14 mmol), thereby dissolving uric acid. Thereafter, a polymer solution was prepared by bubbling nitrogen gas for 5 minutes.

[Michael addition reaction]

A cross-linker solution 3416.4 mg (2.14 mmol) of N,N'-bisacryloylpiperazine (Sigma Aldrich) and 2.9 mg (0.0107 mmol) of 2,2'-azobis(2-amidinopropane) dihydrochloride (Sigma Aldrich) in 2.7 ml of water and bubbling nitrogen gas for 5 minutes. The cross-linker solution was added to the polymer solution described in the above and stirred as such for 30 seconds. After completion of the stirring, the first stage cross-linking reaction by the Michael addition reaction was carried out by allowing this to stand at room temperature for 16 hours in the dark.

[Radical Polymerization Reaction]

Thereafter, the second stage cross-linking reaction by a radical polymerization reaction was carried out by irradiating ultraviolet ray using a black light at 4° C. for 24 hours, thereby obtaining a bulk cross-linked copolymer more rigid than after the first stage cross-linking reaction.

The bulk cross-linked copolymer described in the above was pulverized by a ball mill and then, in order to remove the used uric acid, thoroughly washed with 0.5 mol/l sodium hydroxide aqueous solution. Subsequently, this was washed with water until its pH became 7. After recovering the supernatant fluid by centrifugation (6,000 rpm, 15 minutes), the precipitate was freeze-dried to obtain particles of an acidic water-soluble target substance (uric acid)-selectively adsorbed polymer.

Inventive Example 1-2

Polymer particles were obtained in the same manner as in Inventive Example 1-1 except that uric acid was not blended.

Comparative Example 1-1

[Preparation of Polymer Solution]

To a screw glass test tube, 1.2 ml portion of an aqueous solution of polyallylamine having a molecular weight of 15,000 (mfd. by NITTO BOSEKI) (PALA 15) prepared into 10% by mass and 36.0 mg (0.21 mmol) of uric acid (Sigma Aldrich) were added, and the uric acid was dissolved. Thereafter, a polymer solution was prepared by bubbling nitrogen gas for 5 minutes.

[Michael Addition Reaction]

A cross-linker solution was prepared by dissolving 416.4 mg (2.14 mmol) of N,N'-bisacryloylpiperazine (Sigma Aldrich) and 2.9 mg (0.0107 mmol) of 2,2'-azobis(2-amidinopropane)dihydrochloride (Sigma Aldrich) in 2.7 ml of water and bubbling nitrogen gas for 5 minutes. This cross-linker solution was added to the polymer solution described in the above and stirred as such for 30 seconds. After completion of the stirring, a cross-linking reaction was carried out by allowing this to stand at room temperature for 16 hours in the dark.

The cross-linked copolymer described in the above obtained by carrying out only the first stage cross-linking reaction by Michael addition reaction was pulverized by a ball mill and then, in order to remove the used uric acid, thoroughly washed with 0.5 mol/l sodium hydroxide aqueous solution. Subsequently, this was washed with water until its pH became 7. After recovering the supernatant fluid by centrifugation (6,000 rpm, 15 minutes), the precipitate was freeze-dried to prepare polymer particles.

Comparative Example 1-2

Polymer particles were prepared in the same manner as in Comparative Example 1-1 except that uric acid was not blended.

Reference Example 1-1

Commercially available activated carbon (mfd. by Aldrich; particle size 2 to 12 μm).

[Evaluation of Uric Acid Adsorbing Performance]

A 10 mg portion of particles of each of Inventive Examples 1-1 and 1-2, Comparative Examples 1-1 and 1-2, and Reference Example 1-1 were added to 1 ml of 1 mmol/l of brine containing 0.2 mmol/l of uric acid (Sigma Aldrich). After 16 hours of incubation at room temperature, liquids to be tested were obtained by centrifugation (4,000 rpm, 10 minutes, room temperature). By measuring the absorbance at 290 nm characteristic to uric acid using a spectrophotometer (Beckman Coulter, DU 800) on each obtained liquid to be tested, residual uric acid was determined, and adsorbed amount of uric acid was calculated from the result. The results are shown in Table 1.

As is evident from Table 1, due to formation of a specific recognition site for uric acid in the polymer by the molecular imprinting method and a two-step reaction (Michael addition reaction and radical polymerization reaction), the polymer of Inventive Example 1-1 showed higher uric acid adsorbing performance in comparison with the polymer of Inventive Example 1-2 in which the polymer was prepared using the same resin composition by the two-step reaction without carrying out the molecular imprinting method.

In addition, Comparative example 1-1 in which the polymer was prepared by the molecular imprinting method and Michael addition reaction also showed higher uric acid adsorbing performance in comparison with Comparative Example 1-2 in which the polymer was prepared using the same resin composition by the Michael addition reaction alone without carrying out the molecular imprinting method. Based on these results, it was found that a polymer which shows high adsorbing performance for an acidic water-soluble target substance can be obtained by preparing the polymer by the molecular imprinting method.

On the other hand, the polymers of Comparative Examples 1-1 and 1-2 in which a polymer having amino group was cross-linked with an unsaturated carbonyl cross-linker by the first stage Michael addition reaction alone among the two-step reaction showed lower uric acid adsorption than the polymers of Inventive Examples 1-1 and 1-2 which were cross-linked by the two-step reaction including Michael addition reaction and radical polymerization. Based on this, it was found that a polymer which shows high adsorbing performance for an acidic water-soluble target substance can be obtained by carrying out the cross-linking by the two-step reaction.

[Evaluation of Specific Recognition Performance 1]

A 10 mg portion of particles of each of Inventive Examples 1-1 and 1-2, Comparative Examples 1-1 and 1-2, and Reference Example 1-1 were added to 1 ml of 1 mmol/l of brine containing 0.2 mmol/l of vitamin $B_3$ (nicotinic acid amide) (Sigma Aldrich) which is an essential component for the living body. After 16 hours of incubation at room temperature, liquids to be tested were obtained by centrifugation (4,000 rpm, 10 minutes, room temperature). By measuring the absorbance at 260 nm characteristic to vitamin $B_3$ using a spectrophotometer (Beckman Coulter, DU 800) on the thus obtained liquids to be tested, residual vitamin $B_3$ were determined, and adsorbed amount of vitamin $B_3$ was calculated from the result. The results are shown in Table 1.

As is evident from Table 1, the polymers of Inventive Examples 1-1 and 1-2 and Comparative Examples 1-1 and 1-2 showed low adsorbing performance for vitamin $B_3$ in comparison with Reference Example 1-1. In this case, as shown in Table 1, Reference Example 1-1 showed high adsorbing performance for an acidic water-soluble target substance (uric acid) in comparison with the polymers of Inventive Examples 1-1 and 1-2 in the uric acid adsorbing performance evaluation, and it also showed high adsorbing performance for vitamin $B_3$ which is a living body essential component. Based on these results, it was confirmed that the polymers of Inventive Examples 1-1 and 1-2 show high adsorbing performance for acidic water-soluble target substances and show low adsorbing performance for vitamin $B_3$.

[Evaluation of Specific Recognition Performance 2]

A 10 mg portion of particles of each of Inventive Examples 1-1 and 1-2, Comparative Examples 1-1 and 1-2, and Reference Example 1-1 were added to 1 ml of 1 mmol/l of brine containing 0.08 mmol/l of vitamin $B_2$ (riboflavin) (Sigma Aldrich) which is an essential component for the living body and has a similar structure of uric acid. After 16 hours of incubation at room temperature, liquids to be tested were obtained by centrifugation (4,000 rpm, 10 minutes, room temperature). By measuring the absorbance at 264 nm characteristic to vitamin $B_2$ using a spectrophotometer (Beckman Coulter, DU 800) on the thus obtained liquids to be tested, residual vitamin $B_2$ was determined, and adsorbed amount of vitamin $B_2$ was calculated from the result. The results are shown in Table 1.

As is evident from Table 1, in comparison with Reference Example 1-1, the polymers of Inventive Examples 1-1 and 1-2 showed lower adsorbing performance for vitamin $B_2$ for which a specific recognition site is not formed. In comparison with the polymers of Inventive Examples 1-1 and 1-2, Reference Example 1-1 showed high adsorbing performance for the acidic water-soluble target substance, and it also showed high adsorbing performance for vitamin $B_2$ which is a living body essential component.

In addition, in comparison with the polymers of Comparative examples 1-1 and 1-2 in which the cross-linking was effected by the first stage Michael addition reaction alone, the polymer of Inventive Example 1-1 in which the cross-linking was effected by the two-step reaction including Michael addition reaction and radical polymerization showed low adsorbing performance, so that it was found that high selective adsorbing performance can be provided by the two-step cross-linking.

Based on these results, it was found that the polymers of Inventive Example 1-1 and 1-2 have high specific recognition performance for acidic water-soluble target substance in comparison with the polymers of Comparative examples 1-1 and 1-2, and Reference Example 1-1. That is, it was found that polymers prepared by effecting the cross-linking through the two-step reaction have high specific recognition performance for acidic water-soluble target substance.

In addition, the polymer of Inventive Example 1-1 in which the cross-linking was effected by the molecular imprinting method and two-step reaction showed higher uric acid adsorption in comparison with the polymer of Inventive Example 1-2 in which the cross-linking was effected by the two-step reaction alone. Based on this, it was found that the high adsorbing performance for acidic water-soluble target substance is further improved by combining the molecular imprinting method and two-step reaction.

TABLE 1

| | Cross-linking method | Uric acid adsorption (μmol/10 mg) | Vitamin $B_3$ adsorption (μmol/10 mg) | Vitamin $B_2$ adsorption (μmol/10 mg) |
|---|---|---|---|---|
| Inv. Ex. 1-1 | Molecular imprinting method + two-step reaction* | 0.06850 | 0 | 0.00096 |
| Inv. Ex. 1-2 | Two-step reaction | 0.05943 | 0 | 0.00132 |
| Comp. Ex. 1-1 | Molecular imprinting method + Michael addition reaction alone | 0.05648 | 0 | 0.00490 |
| Comp. Ex. 1-2 | Michael addition reaction alone | 0.04526 | 0 | 0.00357 |
| Ref. Ex. 1-1 | — | 0.07697 | 0.02076 | 0.04045 |

*Two-step reaction: Michael addition reaction + radical polymerization reaction

[Evaluation of Adsorption Rate]

A 10 mg portion of the particles of Inventive Example 1-1 were added to 1 ml of 1 mmol/l of brine containing 0.2 mmol/l of uric acid. After 0.5, 0.7, 3, 11 or 16 hours of incubation at room temperature, each liquid to be tested was obtained by centrifugation (10,000 rpm, 1 minute, room temperature). By measuring the absorbance at 290 nm characteristic to uric acid using a spectrophotometer (Beckman Coulter, DU 800) on the thus obtained liquid to be tested, residual uric acid was determined, and adsorption rate of uric acid was calculated from the result. The results are shown in FIG. 1.

As is evident from FIG. 1, adsorption of the acidic water-soluble target substance is saturated within 1 hour by the polymer of Inventive Example 1-1. Based on this, when the necessity for 3 hours per once in the general blood dialysis therapy is taken into consideration, it is expected that the polymer of the invention can exert quick adsorbing performance.

Inventive Examples 2-1 to 2-9

(Polymers Having Amino Group and/or Imino Group)

An aqueous solution of a polyallylamine having a molecular weight of 3,000 (total amount of amino groups per 1 g, 17.5 mmol) (mfd. by NITTO BOSEKI) (to be referred to as PALA 03 hereinafter), an aqueous solution of a polyallylamine having a molecular weight of 15,000 (total amount of amino groups per 1 g, 17.5 mmol) (mfd. by NITTO BOSEKI) (to be referred to as PALA 15 hereinafter), and a polyallylamine having 2,4-diamino-s-triazine group (to be referred to as DAT group hereinafter) (to be referred to as DAT-PALA hereinafter) were used as the polymers having amino group and/or imino group. DAT-PALA was synthesized as follows.

Synthesis of DAT-PALA

Figure 2:
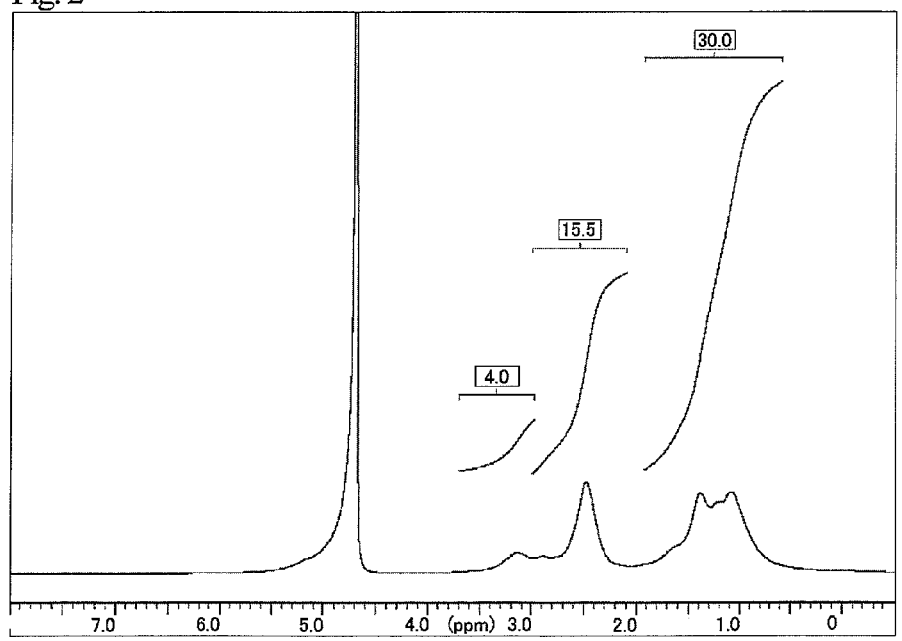
FIG. 2 shows $^1$H-NMR spectrum of DAT-PALA.

A 5 ml portion of PALA 03 (total amount of amino group, 35 mmol) adjusted to 40% by mass, 20 ml of 0.5 mol/l sodium hydroxide aqueous solution and 1.018 mg (7 mmol) of 2,4-diamino-6-chloro-s-triazine (to be referred to as Cl-DAT hereinafter) were put into a flask and mixed with stirring. The DAT-PALA shown by the following formula (7) was synthesized by the ammonolysis reaction of Cl-DAT by rising temperature of the thus obtained mixed liquid to 110° C. and stirring and refluxing it as such for 48 hours. $^1$H-NMR spectrum of the obtained DAT-PALA is shown in FIG. 2.

[Chem. 2]

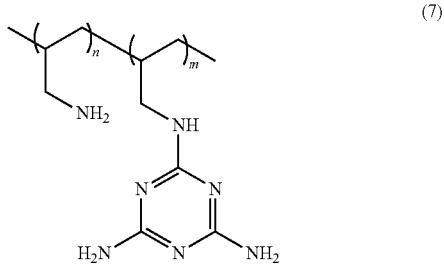

(7)

The solution described in the above was cooled to room temperature and the insoluble matter was removed by filtration. The thus obtained filtrate was passed through 60 ml of a strongly acidic cation exchange resin (Amberlite, IR120, H type) and 60 ml of a strongly basic anion exchange resin (Amberlite, IRA400, OH type) to effect desalting. The DAT-PALA was obtained by freeze-drying the filtrate.

Structure of the thus obtained DAT-PALA was confirmed by IR and $^1$H-NMR. DAT group was introduced into 20 mol % of the total amino groups the polyallylamine described in the above used in the synthesis of DAT-PALA, and the total amount of amino group per 1 g of DAT-PALA was 15.2 mmol.

(Unsaturated Carbonyl Cross-Linker)

As the unsaturated carbonyl cross-linker, N,N'-bisacryloylpiperazine (to be referred to as BAP hereinafter) (Sigma Aldrich) and N,N'-ethylenebisacrylamide (to be referred to as EBAA hereinafter) (Sigma Aldrich) were used.

(Polymerization Initiator)

As the polymerization initiator, 2,2'-azobis(2-amidinopropane)dihydrochloride (Sigma Aldrich) was used.

(Polymerization Solvent)

As the polymerization solvent, ultrapure water was used.

(Template Molecules)

As the template molecules, respective acidic water-soluble target substances uridine 5'-monophosphate (to be referred to as UMP hereinafter) (Sigma Aldrich), adenosine 5'-monophosphate (to be referred to as AMP hereinafter) (Sigma Aldrich), N-carbobenzoxy-L-aspartic acid (to be referred to as ZAsp hereinafter) (Sigma Aldrich) and uric acid (Sigma Aldrich) were used.

Each polymer having the composition shown in Table 2 was prepared by the following procedures.

[Preparation of Polymer Solution]

The template molecule was dissolved by adding to a solution of a polymer having an amino group and/or imino group, which had been prepared into a 10% by mass aqueous solution (DAT-PALA is 13.3% by mass) in a screw test tube made of grass. Thereafter, the polymer solution was prepared by bubbling nitrogen gas thereto for 5 minutes.

[Michael Addition Reaction]

A cross-linker solution was prepared by dissolving an unsaturated carbonyl cross-linker and an polymerization initiator in the polymerization solvent and bubbling nitrogen gas for 5 minutes. This cross-linker solution was added to the polymer solution described in the above, and stirring was carried out as such for 30 seconds. After completion of the stirring, the first stage cross-linking reaction by the Michael addition reaction was carried out by allowing it to stand at room temperature for 16 hours in the dark.

[Radical Polymerization Reaction]

Thereafter, by carrying out the second stage cross-linking reaction through the irradiation of ultraviolet ray using a black light at 4° C. for 24 hours, there was obtained a bulk cross-linked copolymer which was more rigid than that of after the aforementioned first stage cross-linking reaction by Michael addition reaction.

The aforementioned bulk cross-linked copolymer was pulverized by a ball mill and then, in order to remove the used template molecule, thoroughly washed with 0.5 mol/l sodium hydroxide aqueous solution. Subsequently, this was washed with ultrapure water until its pH became 7. After recovering the supernatant fluid by centrifugation (6,000 rpm, 10 minutes), the precipitate was freeze-dried to obtain polymer particles having a specific recognition site for each acidic water-soluble target substance.

Inventive Examples 2-10 to 2-15

As shown in Table 2, the polymer particles having respective compositions shown in Table 2 were obtained by the same methods of Inventive Examples 2-1 to 2-9, except that the template molecules were not blended.

TABLE 2

| | Template molecule | | Polymer having amino group and/or imino group | | Unsaturated carbonyl cross-linker | | Polymerization Initiator | Polymerization solvent |
|---|---|---|---|---|---|---|---|---|
| | | | | Total amino groups | | Total unsaturated carbonyl groups | | |
| | Kind | (mmol) | Kind | (mmol) | Kind | (mmol) | (mmol) | (ml) |
| Inv. Ex. 2-1 | UMP | 0.21 | PALA 03 | 2.14 | BAP | 4.28 | 0.01 | 1.0 |
| Inv. Ex. 2-2 | AMP | 0.21 | PALA 03 | 2.14 | BAP | 4.28 | 0.01 | 1.0 |
| Inv. Ex. 2-3 | Zasp | 0.21 | PALA 03 | 2.14 | BAP | 4.28 | 0.01 | 1.0 |
| Inv. Ex. 2-4 | Uric acid | 0.21 | PALA 03 | 2.14 | BAP | 4.28 | 0.01 | 1.0 |
| Inv. Ex. 2-5 | Uric acid | 0.21 | PALA 15 | 2.14 | BAP | 4.28 | 0.01 | 1.0 |
| Inv. Ex. 2-6 | Uric acid | 0.21 | PALA 03 | 2.14 | BAP | 8.56 | 0.01 | 1.0 |
| Inv. Ex. 2-7 | Uric acid | 0.21 | PALA 03 | 2.14 | BAP | 4.28 | 0.01 | 2.7 |
| Inv. Ex. 2-8 | Uric acid | 0.21 | PALA 15 | 2.14 | EBAA | 4.28 | 0.01 | 2.7 |
| Inv. Ex. 2-9 | Uric acid | 0.21 | DAT-PALA | 2.57 | BAP | 4.28 | 0.01 | 1.0 |
| Inv. Ex. 2-10 | — | — | PALA 03 | 2.14 | BAP | 4.28 | 0.01 | 1.0 |

TABLE 2-continued

| | Template molecule | | Polymer having amino group and/or imino group | | Unsaturated carbonyl cross-linker | | Polymerization Initiator | Polymerization solvent |
|---|---|---|---|---|---|---|---|---|
| | | | | Total amino groups | | Total unsaturated carbonyl groups | | |
| | Kind | (mmol) | Kind | (mmol) | Kind | (mmol) | (mmol) | (ml) |
| Inv. Ex. 2-11 | — | — | PALA 15 | 2.14 | BAP | 4.28 | 0.01 | 1.0 |
| Inv. Ex. 2-12 | — | — | PALA 03 | 2.14 | BAP | 8.56 | 0.01 | 1.0 |
| Inv. Ex. 2-13 | — | — | PALA 03 | 2.14 | BAP | 4.28 | 0.01 | 2.7 |
| Inv. Ex. 2-14 | — | — | PALA 15 | 2.14 | EBAA | 4.28 | 0.01 | 2.7 |
| Inv. Ex. 2-15 | — | — | DAT-PALA | 2.57 | BAP | 4.28 | 0.01 | 1.0 |

Comparative Examples 2-1 to 2-4

In Comparative Examples 2-1 and 2-2, polymers having the compositions shown in Table 3 were prepared by a molecular imprinting method which is generally carried out using a functional monomer. In addition, in Comparative Examples 2-3 and 2-4, conventional cross-linked copolymer particles having the compositions shown in Table 3 were obtained by the same method of Comparative Examples 2-1 and 2-2 except that the template molecule was not blended.

The following were used as the materials of the polymer particles of Comparative Examples 2-1 and 2-2 and of the cross-linked copolymer particles of Comparative Examples 2-3 and 2-4.

Template molecule: uric acid (Sigma Aldrich) as an acidic water-soluble target substance
Functional monomers: allylamine (ALA) (Sigma Aldrich), vinyl imidazole (VID) (Sigma Aldrich)
Cross-linker: EBAA (Sigma Aldrich)
Polymerization initiator 2,2'-azobis(2-amidinopropane)dihydrochloride (Sigma Aldrich)
Polymerization solvent: ultrapure water Ingredient mixed liquid were prepared by dissolving the functional monomer, cross-linker, polymerization initiator and template molecule in the polymerization solvent by the compositions shown in Table 3 and bubbling nitrogen gas for 5 minutes. Thereafter, rigid bulk polymers were obtained by effecting cross-linking reaction through the irradiation of ultraviolet ray using a black light at 4° C. for 24 hours.

Each of the aforementioned bulk cross-linked copolymers was pulverized by a ball mill and then, in order to remove the used template molecules, thoroughly washed with 0.5 mol/l sodium hydroxide aqueous solution. Subsequently, they were washed with ultrapure water until their pH became 7. After recovering the supernatant fluid by centrifugation (6,000 rpm, 15 minutes), the precipitates were freeze-dried to obtain the polymer particles of Comparative Examples 2-1 and 2-2 and, the cross-linked copolymer particles of Comparative Examples 2-3 and 2-4.

TABLE 3

| | Template molecule | | Functional monomer | | Cross-linker | | Polymerization Initiator | Polymerization solvent |
|---|---|---|---|---|---|---|---|---|
| | Kind | (mmol) | Kind | (mmol) | Kind | (mmol) | (mmol) | (ml) |
| Comp. Ex. 2-1 | Uric acid | 0.04 | ALA | 2.57 | EBAA | 2.14 | 0.01 | 2.7 |
| Comp. Ex. 2-2 | — | — | ALA | 2.57 | EBAA | 2.14 | 0.01 | 2.7 |
| Comp. Ex. 2-3 | Uric acid | 0.04 | VID | 2.57 | EBAA | 2.14 | 0.01 | 2.7 |
| Comp. Ex. 2-4 | — | — | VID | 2.57 | EBAA | 2.14 | 0.01 | 2.7 |

[Evaluation of UMP Adsorbing Performance]

A 10 mg portion of particles of each of Inventive Examples 2-1, 2-2, 2-4 and 2-10 were put into respective four tubes of a 2 ml capacity micro tube and 1 ml of 1 mmol/l of brine containing 0.01 mmol/l of UMP was added thereto. After 16 hours of incubation at room temperature, liquids to be tested were obtained by centrifugation (4,000 rpm, 10 minutes, room temperature). By measuring the absorbance at 260 nm characteristic to UMP using a spectrophotometer (Beckman Coulter, DU 800) on the thus obtained liquids to be tested, residual UMP was determined, and adsorbed amount of UMP was calculated from the result.

In addition, the UMP adsorption improving effect provided by the molecular imprinting method was calculated in accordance with the following formula. The results are shown in Table 4.

$UMP$ adsorption improving effect
$(nmol/10\ mg) = A/B$

A: UMP adsorption of Inventive Examples 2-1, 2-2 or 2-4
B: UMP adsorption of Inventive Example 2-10 which has the same resin composition of Inventive Examples 2-1, 2-2 and 2-4

TABLE 4

| | Template molecule Kind | UMP adsorption (nmol/10 mg) | UMP adsorption improving effect |
|---|---|---|---|
| Inv. Ex. 2-1 | UMP | 3.736 | 1.611 |
| Inv. Ex. 2-2 | AMP | 2.538 | 1.094 |

TABLE 4-continued

| | Template molecule Kind | UMP adsorption (nmol/10 mg) | UMP adsorption improving effect |
|---|---|---|---|
| Inv. Ex. 2-4 | Uric acid | 2.648 | 1.142 |
| Inv. Ex. 2-10 | — | 2.319 | 1 |

As is evident from Table 4, the polymer of Inventive Example 2-1 which has a specific recognition site for UMP showed high adsorbing performance for UMP in comparison with the polymers of Inventive Examples 2-2, 2-4 and 2-10 having the same resin composition. Based on this, it was found that further high adsorption effect for acidic water-soluble target substances can be obtained by preparing polymers by the molecular imprinting method.

In addition, the polymer of Inventive Example 2-2 having a specific recognition site for AMP and the polymer of Inventive Example 2-3 having a specific recognition site for uric acid showed a UMP adsorbing performance at similar degree of Inventive Example 2-10 which did not use the molecular imprinting method. Based on this, it was found that polymers show high selective adsorbing performance for acidic water-soluble target substances when a specific recognition site is designed by the molecular imprinting method.

[Evaluation of AMP Adsorbing Performance]

A 10 mg portion of particles of each of Inventive Examples 2-2 and 2-10 were put into respective two tubes of a 2 ml capacity micro tube and 1 ml of 1 mmol/l of brine containing 0.01 mmol/l of AMP was added thereto. After 16 hours of incubation at room temperature, liquids to be tested were obtained by centrifugation (4,000 rpm, 10 minutes, room temperature). By measuring the absorbance at 260 nm characteristic to AMP using a spectrophotometer (Beckman Coulter, DU 800) on the thus obtained liquids to be tested, residual AMP was determined, and adsorbed amount of AMP was calculated from the result.

In addition, the AMP adsorption improving effect provided by the molecular imprinting method was calculated in accordance with the following formula. The results are shown in Table 5.

AMP adsorption improving effect (nmol/10 mg)=$A/B$

A: AMP adsorption of Inventive Examples 2-2
B: AMP adsorption of Inventive Example 2-10 which has the same resin composition of Inventive Examples 2-2

TABLE 5

| | Template molecule Kind | AMP adsorption (nmol/10 mg) | AMP adsorption improving effect |
|---|---|---|---|
| Inv. Ex. 2-2 | AMP | 3.147 | 1.238 |
| Inv. Ex. 2-10 | — | 2.541 | 1 |

As is evident from Table 5, the polymer of Inventive Example 2-2 which has a specific recognition site for AMP showed high adsorbing performance for AMP in comparison with the polymer of Inventive Example 2-10 having the same resin composition. Based on this, it was found that further high adsorption effect for the acidic water-soluble target substance can be obtained by preparing polymer by the molecular imprinting method.

[Evaluation of ZAsp Adsorbing Performance]

A 10 mg portion of particles of each of Inventive Example 3 and Comparative Example 1 were put into respective two tubes of a 2 ml capacity micro tube and 1 ml of 1 mmol/l of brine containing 0.2 mmol/l of ZAsp was added thereto. After 16 hours of incubation at room temperature, liquids to be tested were obtained by centrifugation (4,000 rpm, 10 minutes, room temperature). Residual amount of ZAsp in the thus obtained liquids to be tested was measured using a liquid chromatography under the following conditions, and adsorbed amount of ZAsp was calculated from the result.

The liquid chromatography was carried out under the following conditions. HPLC apparatus: Lachrom system manufactured by Hitachi
Column: Chromolith RP-18e
Flow rate: 0.5 ml/min
Detector: LC 7455 UV 254 nm
Injection amount: 100 µl
Eluent: 0.1% TFA aqueous solution/0.1% acetonitrile=75/25

In addition, the ZAsp adsorption improving effect provided by the molecular imprinting method was calculated in accordance with the following formula. The results are shown in Table 6.

ZAsp adsorption improving effect (nmol/10 mg)=$A/B$

A: ZAsp adsorption of Inventive Examples 2-3
B: ZAsp adsorption of Inventive Example 2-10 which has the same resin composition of Inventive Examples 2-3

TABLE 6

| | Template molecule Kind | ZAsp adsorption (nmol/10 mg) | ZAsp adsorption improving effect |
|---|---|---|---|
| Inv. Ex. 2-3 | ZAsp | 128.6 | 1.18 |
| Inv. Ex. 2-10 | — | 109.0 | 1 |

As is evident from Table 6, the polymer of Inventive Example 2-3 which has a specific recognition site for ZAsp showed high adsorbing performance for ZAsp in comparison with the polymer of Inventive Example 2-10 having the same resin composition. Based on this, it was found that further high adsorption effect for the acidic water-soluble target substance can be obtained by preparing polymer by the molecular imprinting method.

[Evaluation of Uric Acid Adsorbing Performance]

A 10 mg portion of particles of each of Inventive Examples 2-1 and 2-4 to 2-15, and Comparative Examples 2-1 to 2-4 were put into respective 17 tubes of a 2 ml capacity micro tube and 1 ml of 1 mmol/l of brine containing 0.01 mmol/l of uric acid was added thereto. After 16 hours of incubation at room temperature, liquids to be tested were obtained by centrifugation (4,000 rpm, 10 minutes, room temperature). By measuring the absorbance at 290 nm characteristic to uric acid using a spectrophotometer (Beckman Coulter, DU 800) on the thus obtained liquids to be tested, residual uric acid was determined, and adsorbed amount of uric was calculated from the result.

In addition, the uric acid adsorption improving effect provided by the molecular imprinting method was calculated in accordance with the following formula. The results are shown in Table 7.

Uric acid adsorption improving effect (nmol/10 mg)=$A/B$

A: Uric acid adsorption of Inventive Examples 2-1 or 2-4 to 2-9, or Comparative Example 2-1 or 2-3
B: Uric acid adsorption of Inventive Examples 2-10 to 2-15 or Reference Example 2-2 or 2-4 (comparative control), which have the same resin composition of Inventive Examples 2-1 or 2-4 to 2-9, or Comparative Example 2-1 or 2-3

TABLE 7

| | Template molecule | Polymer having amino group and/or imino group or functional monomer | Unsaturated carbonyl cross-linker Kind | Total unsaturated carbonyl groups (mmol) | Polymerization solvent (ml) | Uric acid adsorption (nmol/10 mg) | Uric acid adsorption improving effect | Comparative control |
|---|---|---|---|---|---|---|---|---|
| Inv. Ex. 2-1 | UMP | PALA 03 | BAP | 4.28 | 1.0 | 3.478 | 1.031 | Inv. Ex. 2-10 |
| Inv. Ex. 2-4 | Uric acid | PALA 03 | BAP | 4.28 | 1.0 | 4.048 | 1.200 | Inv. Ex. 2-10 |
| Inv. Ex. 2-5 | Uric acid | PALA 15 | BAP | 4.28 | 1.0 | 4.054 | 1.221 | Inv. Ex. 2-11 |
| Inv. Ex. 2-6 | Uric acid | PALA 03 | BAP | 8.56 | 1.0 | 2.552 | 1.530 | Inv. Ex. 2-12 |
| Inv. Ex. 2-7 | Uric acid | PALA 03 | BAP | 4.28 | 2.7 | 4.608 | 1.234 | Inv. Ex. 2-13 |
| Inv. Ex. 2-8 | Uric acid | PALA 15 | EBAA | 4.28 | 2.7 | 4.195 | 1.185 | Inv. Ex. 2-14 |
| Inv. Ex. 2-9 | Uric acid | DAT-PALA | BAP | 4.28 | 1.0 | 9.133 | 1.515 | Inv. Ex. 2-15 |
| Inv. Ex. 2-10 | — | PALA 03 | BAP | 4.28 | 1.0 | 3.373 | 1 | — |
| Inv. Ex. 2-11 | — | PALA 15 | BAP | 4.28 | 1.0 | 3.320 | 1 | — |
| Inv. Ex. 2-12 | — | PALA 03 | BAP | 8.56 | 1.0 | 1.668 | 1 | — |
| Inv. Ex. 2-13 | — | PALA 03 | BAP | 4.28 | 2.7 | 3.732 | 1 | — |
| Inv. Ex. 2-14 | — | PALA 15 | EBAA | 4.28 | 2.7 | 3.541 | 1 | — |
| Inv. Ex. 2-15 | — | DAT-PALA | BAP | 4.28 | 1.0 | 6.027 | 1 | — |
| Comp. Ex. 2-1 | Uric acid | ALA | — | — | 2.7 | 1.614 | 0.785 | Ref. Ex. 2-2 |
| Comp. Ex. 2-2 | — | ALA | — | — | 2.7 | 2.056 | 1 | — |
| Comp. Ex. 2-3 | Uric acid | VID | — | — | 2.7 | 4.454 | 0.967 | Ref. Ex. 2-4 |
| Comp. Ex. 2-4 | — | VID | — | — | 2.7 | 4.608 | 1 | — |

As is evident from Table 7, the polymers of Inventive Examples 2-4 to 2-9 which have a specific recognition site for uric acid showed high adsorbing performance for uric acid in comparison with the polymers of comparative controls having the same resin composition. In addition, the polymer of Inventive Example 2-1 which has a specific recognition site for UMP showed high adsorbing performance for UMP in comparison with the polymer of Inventive Example 2-4 as shown in Table 4, but it showed low adsorbing performance for uric acid.

Based on these results, it was found that the polymers prepared by the method of the invention have specific recognition sites complementary to respective target substances and show high selective adsorbing performance for acidic water-soluble target substances by the specific recognition sites.

In addition, the cross-linked copolymers of Comparative Examples 2-1 and 2-3 prepared by the molecular imprinting method using functional monomers did not show specific adsorbing performance for uric acid. Based on this, it was found that the polymers prepared by the method of the invention can efficiently perform interaction with template molecules at multiple points and can form specific recognition sites efficiently in the polymers by using the polymer having an amino group and/or imino group.

In this case, the molar ratio of uric acid as the template molecule/functional monomer is 0.02 at the maximum due to poor solubility of uric acid, therefore, it was difficult to increase the number of specific recognition sites existing in the polymer.

In Inventive Example 2-4 in which the (amino group and/or imino group)/(unsaturated carbonyl group of unsaturated carbonyl cross-linker) molar ratio was set to 0.5, the uric acid adsorption improving effect became small in comparison with Inventive Example 2-6 in which the molar ratio was set to 0.25. Based on this, it was found that non-selective adsorption can be suppressed when formation of specific recognition site is accelerated by the rigid cross-linking structure and the amino group/imino group per polymer unit weight is decreased.

The polymer of Inventive Example 2-9 in which both of the amino group and DAT group were used showed higher adsorbing performance for uric acid in comparison with the polymer of Inventive Example 2-15 which has the same resin composition. Based on this, it was found that high specific binding performance can be provided even by a molecular imprinting method which uses two or more functional groups.

In addition, the polymer of Inventive Example 2-9 showed a particularly higher uric acid adsorption improving effect than the polymer of Inventive Example 2-4 in which the amino group alone was used. Based on this, it was found that multiple point and specific interaction with an acidic water-soluble target substance becomes possible when a large number of functional groups capable of interacting with the acidic water-soluble target substance are introduced into the polymer so that high adsorbing performance for the acidic water-soluble target substance can be exerted.

[Evaluation of Specific Adsorption Strength]

A 10 mg portion of particles of each of Inventive Example 2-4, Inventive Example 2-9, Comparative Example 2-1 and Comparative Example 2-6 were put into 2 ml capacity micro tubes and each of 1 ml of 10 mmol/l or 150 mmol/l of brine containing 0.01 mmol/l of uric acid was added thereto. After 16 hours of incubation at room temperature, liquids to be tested were obtained by centrifugation (4,000 rpm, 10 minutes, room temperature). By measuring the absorbance at 290 nm characteristic to uric acid using a spectrophotometer (Beckman Coulter, DU 800) on the thus obtained liquids to be tested, residual uric acid was determined, and adsorbed amount of uric was calculated from the result.

In addition, the uric acid adsorption improving effect provided by the molecular imprinting method was calculated in accordance with the following formula. The results are shown in Table 8.

Uric acid adsorption improving effect at each salt concentration (nmol/10 mg)=$A/B$ A: Uric acid adsorption of Inventive Examples 2-4 or 2-9 at each salt concentration B: Uric acid adsorption of Inventive Example 2-10 or 2-15 (comparative control), which has the same resin composition of Inventive Example 2-4 or 2-9 at each salt concentration

TABLE 8

| | Template molecule | Polymer having amino group and/or imino group | 10 mM brine | | 150 mM brine | | Comparative control |
|---|---|---|---|---|---|---|---|
| | | | Uric acid adsorption (nmol/10 mg) | Uric acid adsorption improving effect | Uric acid adsorption (nmol/10 mg) | Uric acid adsorption improving effect | |
| Inv. Ex. 2-4 | Uric acid | PALA 03 | 0.504 | 2.739 | 0.000 | 0 | Inv. Ex. 2-10 |
| Inv. Ex. 2-9 | Uric acid | DAT-PALA | 7.838 | 2.061 | 5.367 | 3.796 | Inv. Ex. 2-15 |
| Inv. Ex. 2-10 | — | PALA 03 | 0.184 | 1 | 0.000 | 0 | — |
| Inv. Ex. 2-15 | — | DAT-PALA | 3.803 | 1 | 1.414 | 1 | — |

As is evident from Table 8, the amount of uric acid adsorbed by the polymers of Inventive Examples 2-4, 2-9, 2-10 and 2-15 was reduced as the salt concentration in the test liquid was increased. Based on this, it was found that the salt component in the test liquid suppresses nonselective adsorption to the polymer matrix surface.

In addition, the polymer of Inventive Example 2-4 prepared by using a polymer having amino group alone showed reduction of the uric acid adsorption improving effect as the salt concentration in the test liquid was increased. Contrary to this, the polymer of Inventive Example 2-9 prepared by using a polymer having both of amino group and DAT group that can interact with the imido structure showed high uric acid adsorption improving effect.

Based on this, it was found that the polymer prepared by the method of the invention, by introducing a large number of functional groups capable of interacting with an acidic water-soluble target substance, becomes possible to specifically interact with the acidic water-soluble target substance at multiple points and it can exert strong specific adsorbing performance for the acidic water-soluble target substance.

[Evaluation of Selective Adsorption Ability]

A 10 mg portion of particles of each of Inventive Examples 2-9 and 2-15 were put into 2 ml capacity micro tubes and 1 ml of 150 mmol/l of brine containing 0.01 mmol/l of thymine [the following formula (9)] (Sigma Aldrich), theobromine [the following formula (10)] (Sigma Aldrich), theophylline [the following formula (11)] (Sigma Aldrich) or caffeine [the following formula (12)] (Sigma Aldrich), having an analogous structure of uric acid [the following formula (8)], was added thereto. After 16 hours of incubation at room temperature, liquids to be tested were obtained by centrifugation (4,000 rpm, 10 minutes, room temperature).

By measuring the absorbance characteristic to respective uric acid-resembling molecules (thymine; 260 nm, theobromine; 270 nm, theophylline; 270 nm, caffeine; 270 nm) using a spectrophotometer (Beckman Coulter, DU 800) on each of the thus obtained liquids to be tested, each of the residual uric acid-resembling molecules was determined, and molecular weight of each residual uric acid-resembling molecule was calculated from the result. The results are shown in Table 9.

As shown in the following formulae (8) to (12), each uric acid-resembling molecule has a shape similar to uric acid, but the chemical structure and size of each uric acid-resembling molecule are substantially different from those of uric acid.

[Chem. 3]

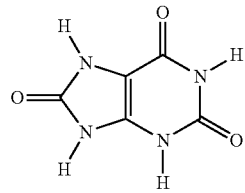

(8)

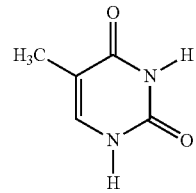

(9)

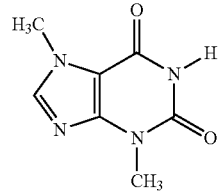

(10)

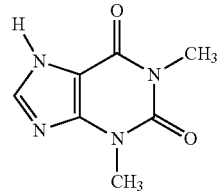

(11)

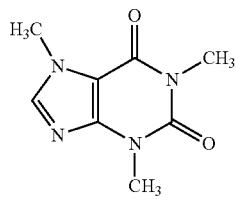

(12)

TABLE 9

| | Template molecule | Adsorption (nmol/10 mg) in 150 mM brine | | | | |
| --- | --- | --- | --- | --- | --- | --- |
| | | Uric acid | Thymine | Theobromine | Theophylline | Caffeine |
| Inv. Ex. 2-9 | uric acid | 5.367 | 0.000 | 0.058 | 0.000 | 0.000 |
| Inv. Ex. 2-15 | — | 1.414 | 0.463 | 0.300 | 0.000 | 0.036 |

As is evident from Table 9, the polymer of Inventive Example 2-9 having a specific recognition site for uric acid showed higher uric acid-adsorbing performance than the polymer of Inventive Example 2-15 having the same resin composition, but showed extremely low adsorbing performance for respective uric acid-resembling molecules (thymine, theobromine, theophylline and caffeine). Based on this, it was found that nonspecific adsorption can be suppressed when DAT group is mainly used in forming a specific recognition site of the polymer for a molecule having the imide structure like uric acid.

That is, it was found that the polymer prepared by the method of the invention, by using a large number of functional groups capable of interacting with an acidic water-soluble target substance, secures a specific recognition site complementary to the acidic water-soluble target substance and it shows high selective adsorbing performance for the acidic water-soluble target substance due to the specific recognition site.

While the invention has been described in detail and with reference to specific embodiments thereof, the invention should not be construed as being limited to the aforementioned embodiments or examples, and modifications, changes and the like can be made therein accordingly.

The present application is based on Japanese Patent Application No. 2008-040189 filed on Feb. 21, 2008, and the contents thereof are incorporated herein by reference.

Industrial Applicability

The acidic water-soluble target substance-adsorbing polymer of the invention exerts the property to more selectively adsorb the acidic water-soluble target substance alone even in a living body-resembling environment, so that it is possible to exclude the acidic water-soluble target substance alone quickly without removing living body essential components. Accordingly, an acidic water-soluble target substance-adsorbing agent including the polymer of the invention as the main component enables suppression of the reduction of blood nutritive components that leads to a complication as well as alleviation of the burden on social activities, in comparison with the conventional blood dialysis, and it is markedly useful as a substitute for the dialysis therapy.

The invention claimed is:

1. A polymer which selectively adsorbs at least one kind of an acidic water-soluble target substance, wherein said polymer has a cross-linked structure formed through a two-step reaction including a Michael addition reaction of a polymer having an amino group and/or imino group with an unsaturated carbonyl cross-linker having at least two unsaturated carbonyl groups, and a subsequent radical polymerization.

2. The polymer according to claim 1, wherein said polymer having an amino group and/or imino group is a polymer modified with at least one kind of a functional group capable of interacting with said acidic water-soluble target substance.

3. The polymer according to claim 2, wherein the functional group capable of interacting with said acidic water-soluble target substance is any one of a diaminotriazine derivative, a diaminopyridine derivative, a guanidine derivative, an imidazole derivative, a porphyrin derivative and a cyclodextrin derivative.

4. The polymer according to claim 1, wherein said acidic water-soluble target substance is any one of a nitrogenous metabolic waste product, nucleotide and an amino acid.

5. The polymer according to claim 4, wherein said nitrogenous metabolic waste product is uric acid.

6. The polymer according to claim 1, wherein a molar ratio of said amino group and/or imino group to said unsaturated carbonyl groups is in a range of from 0.15 to 1.35.

7. The polymer according to claim 1, which selectively adsorbs said acidic water-soluble target substance in an aqueous solution.

8. A process for producing a polymer which selectively adsorbs at least one kind of an acidic water-soluble target substance, wherein said process comprises forming a cross-linked copolymer through a two-step reaction including a Michael addition reaction of at least one kind of a polymer having an amino group and/or imino group and being capable of interacting with said acidic water-soluble target substance with an unsaturated carbonyl cross-linker, and a subsequent radical polymerization.

9. The process for producing a polymer according to claim 8, wherein the polymer having an amino group and/or imino group has, other than the amino group and/or imino group, at least one kind of a functional group capable of partially bonding with said acidic water-soluble target substance.

10. An acidic water-soluble target substance-adsorbing agent which comprises the polymer according to claim 1.

11. A method comprisng selectively separating or removing an acidic water-soluble target substance using the polymer according to claim 1.

12. A polymer containing a specific recognition site for at least one kind of an acidic water-soluble target substance, wherein said specific recognition site is formed in a aqueous solution by a molecular imprinting method including the following steps (1) and (2):

(1) a step of forming a cross-linked copolymer through a two-step reaction, including a Michael addition reaction of at least one kind of a polymer having an amino group and/or imino group and being capable of interacting with said template molecule with an unsaturated carbonyl cross-linker having at least two unsaturated carbonyl groups, and a subsequent radical polymerization, in the presence of at least one kind of a template molecule; and (2) a step of carrying out a release removal of said template molecule from the cross-linked copolymer obtained in the step (1), thereby forming the specific recognition site for said template molecule.

13. The polymer according to claim 12, wherein said template molecule is an acidic water-soluble target substance or a dummy molecule of said acidic water-soluble target substance.

14. The polymer according to claim 12, wherein said polymer having an amino group and/or imino group is a polymer modified with at least one kind of a functional group capable of interacting with said acidic water-soluble target substance.

15. The polymer according to claim 14, wherein the functional group capable of interacting with said acidic water-soluble target substance is any one of a diaminotriazine derivative, a diaminopyridine derivative, a guanidine derivative, an imidazole derivative, a porphyrin derivative and a cyclodextrin derivative.

16. The polymer according to claim 12, wherein said acidic water-soluble target substance is any one of a nitrogenous metabolic waste product, nucleotide and an amino acid.

17. The polymer according to claim 16, wherein said nitrogenous metabolic waste product is uric acid.

18. The polymer according to claim 12, wherein a molar ratio of said amino group and/or imino group to said unsaturated carbonyl groups is in a range of from 0.15 to 1.35.

19. The polymer according to claim 12, which is capable of partially bonding with the acidic water-soluble target substance through said specific recognition site.

20. The polymer according to claim 12, which selectively adsorbs said acidic water-soluble target substance in an aqueous solution.

21. A process for producing a polymer containing a specific recognition site for at least one kind of an acidic water-soluble target substance, said process comprising forming the specific recognition site in an aqueous solution by a molecular imprinting method including the following steps (1) and (2):

(1) a step of forming a cross-linked copolymer through a two-step reaction including a Michael addition reaction of at least one kind of a polymer having an amino group and/or imino group and being capable of interacting with said template molecule with an unsaturated carbonyl cross-linker, and a subsequent radical polymerization, in the presence of at least one kind of a template molecule; and (2) a step of carrying out a release removal of said template molecule from the cross-linked copolymer obtained in the step (1), thereby forming the specific recognition site for said template molecule.

22. The process for producing a polymer according to claim 21, wherein the polymer having an amino group and/or imino group has, other than the amino group and/or imino group, at least one kind of a functional group capable of partially bonding with said acidic water-soluble target substance.

23. An acidic water-soluble target substance-adsorbing agent which comprises the polymer according to claim 12.

24. A method comprising selectively separating or removing an acidic water-soluble target substance using the polymer according to claim 12.

* * * * *